United States Patent [19]

Fuisz

[11] Patent Number: 5,407,676

[45] Date of Patent: * Apr. 18, 1995

[54] HYDROPHILIC FORM OF PERFLUORO COMPOUNDS AND A METHOD OF MANUFACTURE

[75] Inventor: Richard C. Fuisz, Great Falls, Va.

[73] Assignee: Fuisz Technologies Ltd., Chantilly, Va.

[*] Notice: The portion of the term of this patent subsequent to Mar. 23, 2010 has been disclaimed.

[21] Appl. No.: 997,300

[22] Filed: Dec. 24, 1992

Related U.S. Application Data

[63] Continuation-in-part of Ser. No. 627,693, Dec. 14, 1990, Pat. No. 5,196,199.

[51] Int. Cl.⁶ .............. A61K 47/26; A61K 31/02; A61K 31/025; A61K 9/10
[52] U.S. Cl. .................... 424/401; 424/484; 424/400; 514/832; 514/844; 514/873
[58] Field of Search .......... 424/401, 484, 400; 514/832, 844, 873

[56] References Cited

U.S. PATENT DOCUMENTS

| | | | |
|---|---|---|---|
| 2,826,169 | 3/1958 | Le Veen | 119/1 |
| 2,918,404 | 12/1959 | Mende et al. | 167/58 |
| 3,019,745 | 2/1962 | Du Bois et al. | 107/8 |
| 3,036,532 | 5/1962 | Bowe | 107/8 |
| 3,067,743 | 12/1962 | Merton et al. | 128/270 |
| 3,070,045 | 12/1962 | Bowe | 107/8 |
| 3,073,262 | 1/1963 | Bowe | 107/8 |
| 3,095,258 | 6/1963 | Scott | 18/54 |
| 3,131,428 | 5/1964 | Mika | 18/8 |
| 3,308,221 | 3/1967 | Opfell | 264/174 |
| 3,324,061 | 6/1967 | Tanquary et al. | 260/29.2 |
| 3,557,717 | 1/1971 | Chivers | 107/54 |
| 3,595,675 | 7/1971 | Ash et al. | 99/130 |
| 3,615,671 | 10/1971 | Schoaf | 99/78 |
| 3,625,214 | 12/1971 | Higuchi | 128/260 |
| 3,723,134 | 3/1973 | Chivers | 99/134 |

(List continued on next page.)

FOREIGN PATENT DOCUMENTS

| | | |
|---|---|---|
| 0307087 | 8/1988 | European Pat. Off. . |
| WO89/08459 | 3/1989 | European Pat. Off. . |
| WO90/06969 | 11/1989 | European Pat. Off. . |
| WO91/18613 | 12/1991 | European Pat. Off. . |
| 2940184 | 10/1979 | Germany . |
| 88/2770 | 4/1988 | South Africa . |
| 88/2771 | 4/1988 | South Africa . |
| 89/9318 | 12/1989 | South Africa . |
| 90/2139 | 3/1990 | South Africa . |
| 90/8406 | 8/1991 | South Africa . |

OTHER PUBLICATIONS

Massoud Kazemzadeh, Ph.D., *Food Process Design Developing Product Through Extrusion* (Jul. 1992).

Robert Geyer, "Blood Replacement Preparations,"—Encyclopedia of *Chemical Technology*, Kirk-Othmer, Third Edition, pp. 159–171.

R. K. Strong, "Oils," *Kingzett's Chemical Encyclopedia*, pp. 686–690.

R. K. Strong, "Waxes," *Kingzett's Chemical Encyclopedia*, pp. 1048, 1050.

*Primary Examiner*—Edward J. Webman
*Attorney, Agent, or Firm*—Hoffmann & Baron

[57] ABSTRACT

Perfluoro compounds such as $C_{12}F_{20}$; $C_{12}F_{27}N$; $C_{12}F_{26}O$; $C_8F_{17}Br$; and $C_{14}F_{24}$ are rendered dispersible colloidally in water or other polar media without the aid of an emulsifying agent by providing a matrix formed by subjecting a feedstock containing perfluoro compounds and carrier materials to conditions which alter the physical and/or chemical structure of the carrier material. The matrix suspends the perfluoro compounds for delivery to a dispersible medium. Thus, a family of new colloidal perfluoro compounds is produced. Methods of producing readily dispersible perfluoro compounds in the absence of emulsifying agents and cosmetics including the same are also disclosed.

24 Claims, No Drawings

U.S. PATENT DOCUMENTS

| | | | |
|---|---|---|---|
| 3,762,846 | 10/1973 | Chivers | 425/7 |
| 3,818,229 | 6/1974 | Long | 250/312 |
| 3,856,443 | 12/1974 | Salvi | 425/9 |
| 3,875,300 | 4/1975 | Homm et al. | 424/28 |
| 3,925,525 | 12/1975 | LaNieve | 264/40 |
| 3,930,043 | 12/1975 | Warning et al. | 426/515 |
| 3,951,821 | 4/1976 | Davidson | 252/1 |
| 3,967,623 | 7/1976 | Butterworth et al. | 128/287 |
| 3,972,725 | 8/1976 | Nicol | 127/58 |
| 3,975,512 | 8/1976 | Long | 424/5 |
| 3,992,265 | 11/1976 | Hansen | 195/127 |
| 4,073,879 | 2/1978 | Long | 424/5 |
| 4,090,920 | 5/1978 | Studer, Jr. | 195/127 |
| 4,136,145 | 1/1979 | Fuchs et al. | 264/164 |
| 4,153,512 | 5/1979 | Messner et al. | 195/103.5 K |
| 4,293,570 | 10/1981 | Vadasz | 426/3 |
| 4,303,684 | 12/1981 | Pitchon et al. | 426/312 |
| 4,371,516 | 2/1983 | Gregory et al. | 424/22 |
| 4,376,743 | 3/1983 | Dees | 264/103 |
| 4,486,417 | 12/1984 | Sugimoto et al. | 424/180 |
| 4,492,685 | 1/1985 | Keith et al. | 424/28 |
| 4,496,592 | 1/1985 | Kuwahara et al. | 426/5 |
| 4,500,546 | 2/1985 | Turbak et al. | 514/781 |
| 4,526,525 | 7/1985 | Oiso et al. | 425/9 |
| 4,585,797 | 4/1986 | Cioca | 514/773 |
| 4,619,833 | 10/1986 | Anderson | 426/548 |
| 4,793,782 | 12/1988 | Sullivan | 425/7 |
| 4,855,326 | 8/1989 | Fuisz | 514/777 |
| 4,865,836 | 9/1989 | Long | 424/5 |
| 4,873,085 | 10/1989 | Fuisz | 424/400 |
| 4,885,281 | 12/1989 | Hanstein et al. | 514/53 |
| 4,900,824 | 2/1990 | Dandliker et al. | 544/185 |
| 4,978,537 | 12/1990 | Song | 426/5 |
| 4,987,154 | 1/1991 | Long | 514/772 |
| 4,997,856 | 3/1991 | Fuisz | 514/777 |
| 5,011,532 | 4/1991 | Fuisz | 106/215 |
| 5,028,632 | 7/1991 | Fuisz | 514/772 |
| 5,034,421 | 7/1991 | Fuisz | 514/772 |
| 5,096,492 | 3/1992 | Fuisz | 106/215 |
| 5,196,199 | 3/1993 | Fuisz | 424/401 |

HYDROPHILIC FORM OF PERFLUORO COMPOUNDS AND A METHOD OF MANUFACTURE

This application is a continuation-in-part application of U.S. application Ser. No. 627,693, filed Dec. 14, 1990, which issued as U.S. Pat. No. 5,196,199 on Mar. 23, 1993.

BACKGROUND OF THE INVENTION

The present invention relates to hydrophilic substances containing perfluoro compounds and to methods of making emulsions containing perfluoro compounds.

In the U.S. Pat. No. 4,855,326, issued Aug. 8, 1989 various substances having pharmacological properties were combined with a sugar and spun into fibers to produce a readily water-soluble product. The various examples enumerated in the patent all involved the use of water soluble medicaments and were directed to enhancing the solubility rate of the different substances. The patent describes methods for combining a medicament with any one or more of the water soluble melt spinnable sugars and spinning the combination to produce a readily soluble floss form of the medicament. The disclosure of such patent is incorporated herein by reference.

In U.S. Pat. No. 5,011,532, the disclosure deals with oleaginous substances such as vegetable oil, baby oil, olive oil, margarine, lanolin, cocoa butter, and the like, and how their lack of affinity for water is altered by mixing the oleaginous substance with sugar and melt spinning the mixture in a cotton candy spinning machine or the equivalent. As so modified the products disperse autogenously in water forming a colloidal or pseudo-colloidal dispersion. Such modification enabled such widely disparate procedures as: (a) incorporating shortening oil in a cake mix containing flour but no egg to which water is added to produce a batter; and (b) producing a confection or medicated lozenge by dehydrating the dispersion and allowing the melted residue to solidify. The aforementioned application discloses that any oleaginous substance that can be mixed with a melt-spinnable sugar, when spun in a cotton candy spinning machine, produces a product which, when added to water or has water added to it, forms, virtually autogenously, a uniform dispersion having all the appearances of a colloidal dispersion. The disclosure of such application is incorporated herein by reference.

Other disclosures relating to spinning substances with one or more sugars will be found in U.S. Pat. Nos. 4,873,085; 5,034,421; 5,028,632; and 4,997,856.

In U.S. Pat. No. 5,034,421, it is explained that a spun product from a combination of a saccharide and a hydrophobic ingredient is hydrophilic with low concentrations of such ingredient but becomes increasingly hydrophobic as the concentration of the hydrophobic ingredient is increased, although the end product nevertheless acts hydrophilically when the water temperature is elevated. Beeswax is disclosed as being a moderating agent. As described therein, pure white pharmaceutical grade beeswax, a substance that is essentially hydrophobic, was mixed with sucrose and spun, producing an excellent floss which floated when added to normal room temperature water, but immediately dispersed with the appearance of being colloidal when added to water at about 180° F. (82.2° C).

In the *Kirk-Othmer Encyclopedia of Chemical Technology*, 3rd ed., Suppl. Vol.—Alcohol Fuels to Toxicology, published by John Wiley & Sons, Corp. 1984, there appears, on pp. 159-171, an article entitled "Blood-Replacement Preparations" by Robert Geyer of Harvard University. The article deals with liquid perfluoro compounds which have been investigated for biomedical application. These nonpolar materials dissolve appreciable quantities of gases such as oxygen and carbon dioxide. The article lists 18 different compounds in a table on page 162 which compounds are identified as suitable for blood-replacement preparations. Among the compounds mentioned are: the perfluoro derivatives of dimethyladamantane, formula $C_{12}F_{20}$; tributylamine, formula $C_{12}F_{27}N$; dihexyl ether, formula $C_{12}F_{26}O$; and 1-bromooctane, formula $C_8F_{17}Br$. All of the mentioned perfluoro compounds are colorless and odorless liquid organic compounds in which all hydrogens have been replaced with fluorine. They are essentially insoluble in water and other polar liquids. To provide a perfusion liquid the perfluoro compound has to be emulsified and this has required an emulsifying agent. The emulsifying agents must be strictly nontoxic for biomedical use. Frequently used emulsifying agents are phospholipids such as egg-yolk phospholipids.

A proprietary product, "Pluronic F-68" produced by BASF Wyandotte Corp., is mentioned in the above article, and stated to be the most frequently used surfactant for blood-replacement preparations. However, the article states that the purified form of the surfactant must be stored at $-25°$ C. or lower, preferably under nitrogen. The restriction on utility should be self-evident.

Use of the egg-yolk phospholipids has encountered problems in that experiments have uncovered a high rate of adverse human reaction to the phospholipids. Thus, prior to the present invention it has not been possible to produce a satisfactory invivo perfusion liquid suitable for transfusion which is based on a perfluoro compound.

SUMMARY OF THE PRESENT INVENTION

It is, therefore, an object of the present invention to provide a perfusion product containing a perfluoro compound but no emulsifying agent which product when added to aqueous media disperses therein without the aid of an emulsifying agent to form a colloidal or pseudo-colloidal dispersion.

Other objects of the present invention are to provide an in vivo perfusion liquid containing a perfluoro compound in colloidal or pseudo-colloidal dispersion throughout a dispersing medium but without the presence of an emulsifying agent, and a method for producing such an in vivo perfusion liquid.

Another object of the present invention is to provide a hydrophilic form of a perfluoro compound which disperses readily in a dispersing medium to form a colloidal dispersion which can be incorporated economically and efficiently in conventional carrier agents for topical application.

In accordance with one aspect of the present invention there is provided a perfusion product which comprises a matrix formed by subjecting a feedstock containing a perfluoro compound and a carrier material to conditions of temperature and shear sufficient to induce flash flow and which alter the physical and/or chemical structure of the carrier material.

In accordance with a further aspect of the present invention, there is provided a matrix which includes one or more saccharides and/or cellulose materials that are readily water-soluble, and a perfluoro compound that in its separate state is essentially insoluble in water and other polar liquids, the perfluoro compound being distributed on, incorporated in, or carried outside the matrix such that when added to any aqueous medium the matrix will disperse therein to form a colloidal or pseudo-colloidal dispersion.

In yet another aspect of this invention, a cosmetic composition is provided by adding a cosmetic ingredient to the feedstock material which also comprises a carrier material and a perfluoro compound. The feedstock material comprising the cosmetic ingredient is then subjected to conditions which alter the physical and/or chemical structure of the carrier material. A cosmetic composition may also be provided by admixing a cosmetic ingredient with the perfusion product of the invention.

In accordance with another aspect of the present invention there is provided a method for producing a perfusion product containing a perfluoro compound, comprising in combination the steps of subjecting a feedstock material comprising a carrier material and a perfluoro compound to conditions which alter the physical and/or chemical structure of the carrier material to form a perfusion product which upon addition to a dispersing medium disperses colloidally or pseudo-colloidally throughout an aqueous medium without employing an emulsifying agent.

The invention will be better understood after reading the following detailed description of the presently preferred embodiments thereof.

DETAILED DESCRIPTION OF THE INVENTION

In the present invention, a rapidly dispersible perfusion product is formed by subjecting a feedstock material comprising a carrier material and a perfluoro compound to conditions of temperature and shear to form a matrix, which when added to a dispersing medium free from an emulsifying agent forms a colloidal dispersion.

For example feedstock material can be processed by subjecting it to high speed spinning on a spinning head in which the substance is also subjected to heating against a heating element. The change of temperature is quite large, which is believed to be occasioned by the spinning head quickly and efficiently spreading the feedstock material against the heating element circumferentially disposed around the perimeter of the spinning head. Thus, extensive surface contact of the feedstock is provided against the heating element itself while being spun.

The feedstock material is heated sufficiently to create an internal flow condition which permits part of the feedstock to move at a subparticle level with respect to the rest of the mass and exit openings provided in the perimeter of the spinning head. The centrifugal force created in the spinning head flings the flowing feedstock material outwardly from the head so that it reforms with a changed structure. The force required to separate and discharge flowable feedstock is only the centrifugal force which results from the spinning head. This describes one approach to producing a novel matrix material.

The spinning process is carried out with "cotton candy" fabricating-type equipment. The floss spinning machine used herein can be any cotton candy-type machine such as the Econo Floss model 3017 manufactured by Gold Medal Products Company of Cincinnati, Ohio. It will be appreciated by those skilled in the art from the present description that any apparatus or physical process which provides similar forces and temperature gradient conditions can also be used. For simplicity in disclosing and describing this invention, the term "melt-spinning" will be understood to mean a flash-flow process which includes a combination of temperature, shear, flow, flow rate, mechanical forces and thermal gradients of the type used in a cotton candy-type machine. The apparatus is operated at a temperature and speed which permits flash flow but does not deteriorate the material undergoing the processing. Usually the resulting matrix product is in the form of a particle, flake, spicule, or other generally non-descript aggregate capable of subsequent processing in accordance with generally accepted techniques.

The melt-spinning process for producing the matrix of the invention includes melting a feedstock material containing the carrier material and a perfluoro compound and forcing the ingredients through the apertures of a grid under conditions of high temperature and shear as disclosed above. The extremely short amount of time the ingredients are exposed to the melt-spinning temperature and shear allows the matrix to be formed without adverse effects.

Unless otherwise indicated, the temperature of the grid in the spinning machine was estimated to be at about 180° F. (82.2° C.) or somewhat higher while operating at a speed of about 3800 R.P.M. Under static conditions, assuming that the grid is stationary and out of contact with the carrier material, the grid temperature was estimated to be at about 500° F. (260° C.)

The flash flow process contemplates subjecting a carrier material to a melt-spin process (or conditions comparable thereto) which provide sufficient internal flow to permit the transition in structure without degradation of the material. Internal flow occurs when the infrastructure of the material breaks down sufficiently to permit movement of material at a subparticle level, and probably at a molecular level. At a molecular level, internal flow contemplates the movement of molecules relative to each other.

Internal flow of material is generally associated with melting point or glass transition point. However, it is contemplated that the combined application of heat and external force is sufficient to produce the flow at temperatures below the melting or glass transition point for most compositions.

For example, another embodiment includes a matrix prepared by raising the temperature of feedstock materials, which includes a non-solubilized carrier, to a point where the carrier undergoes internal flow upon application of a fluid shear force. The feedstock is subjected to disruptive fluid shear force to form multiple parts or masses which have a morphology different from that of the original feedstock. The multiple masses are cooled substantially immediately after contact with the fluid shear force and are permitted to continue in a free-flow condition until solidified.

The perfluoro compounds included in the feedstock material are perfluoro derivatives of dimethyladamantane, tributylamine, dihexyl ether, and 1-bromooctane. These are colorless and odorless liquid organic compounds in which all hydrogens have been replaced with fluorine. Because of their enhanced oxygen carrying capacity, all these compounds have been successfully used in preparations of blood substitutes.

To provide a perfusion product the perfluoro compound must be emulsified. By using the matrix of the invention, when the perfusion product of the invention is added to a dispersing medium, such as water, acetic acid, polar organic solvents or other suitable blood transfusion medium, then the product forms a colloidal dispersion in the absence of any emulsifying agent.

The carriers included in the matrix are preferably saccharide-based and/or water-soluble cellulosic materials or mixtures thereof. A non-limiting list of suitable saccharide carriers include sucrose, lactose, fructose, dextrose, sorbitol, mannitol, fructose, maltose, synthetically-derived saccharide materials such as polydextrose, and the like and mixtures thereof. Alternative saccharide materials such as maltodextrins and/or corn syrup solids are also useful. Suitable water-soluble cellulosic materials include methylcellulose, ethylcellulose, hydroxymethyl or hydroxyethylcellulose, alkali-metal salts of carboxymethylcelluloses and the like and mixtures thereof.

In one embodiment, the present invention also includes cosmetic products, i.e., those products which include ingredients having cosmetic activity. Such products can be used for treating hair or skin cosmetically. The active ingredient can be included (1) within the matrix, (2) outside the matrix, or (3) be incorporated in the product both inside and outside the matrix. A non-limiting list of ingredients which have cosmetic activity includes dimethyl siloxanes, mucopolysaccharide, methyl and propyl parabens, biotin, lanolin, aloe, glycerin, nicotinamide compounds, sun screen, such as paraaminobenzoic acid, hair conditioner, moisturizing creams, astringents, and combinations thereof. Additives, such as coloring agents, surfactants, dispersing aids, adhesion promoters, flavors, sweeteners, dyes, preservatives and mixtures thereof can be included in the cosmetic composition comprising the perfusion product based matrix of the invention.

The invention can be further understood by considering a number of examples. The following examples serve to provide further appreciation of the invention but are not meant to restrict the effective scope of the invention in any way.

EXAMPLE I

One part by volume perfluorooctylbromide marketed by Alliance Pharmaceutical Corp., of San Diego, Calif. under the trademark "Imagent GI" was mixed with three parts by volume sucrose. It was mixed with a spoon in a glass vessel for about 5 minutes. The mixture was then spun using the Econo Floss spinning machine. A quantity of floss was produced. When some of this floss was added to a quantity of water at room temperature, the floss immediately dispersed in the water producing a mild to moderate Tyndahl effect characteristic of a colloidal dispersion. Examination by microscope at a magnification of about 1200X reveals complete colloidal dispersion with the suspended particles averaging about 2 microns or less.

The "Imagent GI" material is supplied as a clear liquid which is intended to be taken orally undiluted prior to an NMR examination of the G.T. tract. Alliance Pharmaceutical also has for limited experimental use a colloidal dispersion form of perfluorooctylbromide intended for intravenous application. This form consists of equal quantities of perfluorooctylbromide and distilled water with sufficient egg yolk phospholipid to cause a complete dispersion. But, as explained previously, the egg yolk phospholipid causes adverse systemic reactions limiting the use of such product. By contrast, the colloidal dispersion that is produced from the floss prepared in the present example, if dispersed in distilled water, can be given intravenously with none of the heretofore involved risks of an adverse reaction otherwise associated with the presence of the phospholipid. Another name for this perfluoro compound is perfluoro 1-bromooctane having the formula, $C_8F_{17}Br$, and known by the abbreviation, FOB.

EXAMPLE II

Example I was repeated substituting for the sucrose an equal quantity of dextrose obtained from Sigma Chemical Co. of St. Louis, Mo. The results were essentially the same.

EXAMPLE III

The following compounds were obtained under generic labeling:

| Perfluoro derivative of | abbreviation | Formula |
| --- | --- | --- |
| dimethyladamantane | FDMA | $C_{12}F_{20}$ |
| tributylamine | FC-43 | $C_{12}F_{27}N$ |
| dihexyl ether | FHE | $C_{12}F_{26}O$ |

Each of the above compounds was mixed with sucrose in the same ratio as in Example I and spun into a floss with the same result. That is, an otherwise immiscible perfluoro compound was rendered miscible in water by spinning with sucrose.

The perfluoro compounds involved in the examples set forth above are representative of the entire class of such compounds identified in the above-mentioned article by Robert Geyer. All of the other perfluoro compounds identified in said article should spin with sucrose or dextrose in the same manner as described in Examples I, II and III hereof.

EXAMPLE IV 10 cc. of perfluoro (tetradecahydrophenanthrene) $C_{14}F_{24}$, from PCR Inc. of Gainsville, Fla. was added to 150 gm. of sucrose which was then mixed thoroughly. The resultant mixture was spun using the Econo Floss spinning machine identified above to produce a nice floss.

Next, 10 gm. of the floss was dispersed in 10 gm. of distilled water by stirring with a pipette. Then 5 drops of the liquid mixture were placed on a glass slide over which was placed a coverglass. Optical examination of the sample on the slide was accomplished using an Olympus Bh2 microscope. Particles were observed ranging in size from 0.2 microns to 2 microns.

EXAMPLE V

Example IV was repeated using the perfluorooctylbromide of Example I instead of the perfluoro (tetradecahydrophenanthrene). Similar particle sizes were obtained in the dispersions.

From the foregoing it should be appreciated that any of the mentioned perfluoro compounds can be spun with a saccharide or a water soluble cellulose material to produce a floss which when added to distilled water can safely be administered intravenously. However, the colloidal dispersions produced from perfluoro compounds in the manner discussed above can also be incorporated in sundry carrier agents such as emollients, cosmetic creams and lotions for topical application where the perfluoro compound can release oxygen to the skin. For lanolin or oil based cosmetics or topical medicaments conventional homogenization techniques can be used, while for water based substances the dispersions can be added directly without any additional emulsifying agents or homogenization.

Having described the present invention with reference to the presently preferred embodiments thereof, it will be apparent to those skilled in the subject art that various changes and modifications can be incorporated without departing from the true spirit of the invention as defined in the appended claims.

What is claimed is:

1. A readily dispersible perfusion product comprising a matrix formed by subjecting a feedstock material comprising a carbohydrate carrier material and a perfluoro compound to flash-flow conditions which alter the physical and/or chemical structure of said carrier material to form said matrix, wherein said product is water dispersible, such that when said product is added to a dispersing medium which is free from any emulsifying agent, a colloidal dispersion is formed.

2. The perfusion product of claim 1, wherein said perfluoro compound is selected from the group consisting of perfluoro derivatives of dimethyladamantane, perfluoro derivatives of tributylamine, perfluoro derivatives of dihexyl ether, perfluoro derivatives of 1-bromooctane, perfluoro derivatives of tetradecahydrophenanthrene, and combinations thereof.

3. The perfusion product of claim 1, wherein the carrier material is selected from the group consisting of monosaccharides, disaccharides and water-soluble polysaccharides.

4. The perfusion product of claim 3, wherein said saccharides are selected from the group consisting of polydextrose, maltodextrins, sucrose, lactose, dextrose, mannitol, sorbitol, glucose, maltose and mixtures thereof.

5. The perfusion product of claim 3, wherein said cellulose materials are selected from the group consisting of methylcellulose, ethylcellulose, hydroxymethylcellulose, hydroxy-ethycellulose, alkaline methyl salts of carboxy-methylcellulose and mixtures thereof.

6. A cosmetic product including a readily dispersible perfusion product comprising a matrix formed by subjecting a feedstock material including a carbohydrate carrier material and a perfluoro compound to flash-flow conditions which alter the physical and/or chemical structure of said carrier material to form said matrix, wherein said product is water-dispersible, such that when said product is added to a dispersing medium which is free from any emulsifying agent, a colloidal dispersion is formed, wherein said feedstock material further comprises a cosmetic ingredient.

7. The cosmetic composition of claim 6, wherein said cosmetic ingredient is selected from the group consisting of dimethyl siloxanes, mucopolysaccharides, methyl paraben, propyl paraben, biotin, lanolin, aloe, mineral oil, nicotinamide compounds, sun screens, hair conditioners, moisturizing agents, astringents, cosmetic powders and mixtures thereof.

8. The cosmetic composition of claim 6, wherein said feedstock material further comprises a member selected from the group consisting of, dispersing aids, adhesion promoters, flavors, sweeteners, dyes, preservatives and mixtures thereof.

9. A cosmetic composition comprising an admixture of a cosmetic ingredient and a readily dispersible perfusion product including a matrix formed by subjecting a feedstock material comprising a carbohydrate carrier material and a perfluoro compound to flash-flow conditions which alter the physical and/or chemical structure of said carrier material to form said matrix, wherein said product is water-dispersible, such that when a product is added to dispersing medium which is free from any emulsifying agent, a colloidal dispersion is formed.

10. The composition of claim 9, wherein said cosmetic ingredient is selected from the group consisting of dimethyl siloxanes, mucopolysaccharides, methyl paraben, propyl paraben, biotin, lanolin, aloe, mineral oil, nicotinamide compounds, sun screens, hair conditioners, moisturizing agents, astringents, cosmetic powders and mixtures thereof.

11. The cosmetic composition of claim 10, wherein said feedstock material further comprises a member selected from the group consisting of, dispersing aids, adhesion promoters, flavors, sweeteners, dyes, preservatives and mixtures thereof.

12. A colloidally dispersible matrix formed by subjecting to flash-flow conditions a feedstock material including a mixture of carbohydrate carrier material and a perfluoro compound wherein said perfluoro compound is devoid of an emulsifying agent and is colloidally dispersible in a dispersing medium without the aid of an emulsifying agent.

13. A perfusion product comprising a spun combination of a perfluoro compound and a carbohydrate carrier material, said combination spun into said product that is water-dispersible, such that when said combination is added to an aqueous medium which is free of an emulsifying agent, a colloidal dispersion is formed.

14. A method of preparing a readily dispersible perfusion product comprising providing a matrix formed by subjecting a feedstock material comprising a carbohydrate carrier material and a perfluoro compound to flash-flow conditions which alter the physical and/or chemical structure of said carrier material to form said product which is water-dispersible, such that upon addition to a dispersing medium free from any emulsifying agent said product forms a colloidal dispersion in the dispersing medium.

15. The method of claim 14, wherein said perfluoro compound is selected from the group consisting of perfluoro derivatives of dimethyladamantene, perfluoro derivatives of tributylamine, perfluoro derivatives of dihexyl derivatives of tetradecahydrophenanthrene, and combinations thereof.

16. The method of claim 14, wherein the carrier material is selected from the group consisting of monosaccharides, disaccharides and water-soluble polysaccharides.

17. The method of claim 16, wherein said saccharides are selected from the group consisting of polydextrose, maltodextrins, sucrose, lactose, dextrose, mannitol, sorbitol, glucose, maltose and mixtures thereof.

18. The method of claim 16, wherein said cellulose materials are selected from the group consisting of methylcellulose, ethylcellulose, hydroxmethylcellulose, hydroxy-ethycellulose, alkaline methyl salts of carboxymethylcellulose and mixtures thereof.

19. A method of providing a cosmetic composition comprising preparing a readily dispersible perfusion product which comprises providing a matrix formed by subjecting a feedstock material comprising a carbohydrate carrier material and a perfluoro compound to flash-flow conditions which alter the physical and/or chemical structure of said carrier material to form said product which is water-dispersible, such that upon addition to a dispersing medium free from any emulsifying agent, said product forms a colloidal dispersion in the dispersing medium, wherein said feedstock material further comprises a cosmetic ingredient.

20. The method of claim 19, wherein said cosmetic ingredient is selected from the group consisting of dimethyl siloxanes, mucopolysaccharides, methyl paraben, propyl paraben, biotin, lanolin, aloe, mineral oil, nicotinamide compounds, sun screens, hair conditioners, moisturizing agents, astringents, cosmetic powders and mixtures thereof.

21. The method of claim 19, wherein said feedstock material further comprises a member selected from the group consisting of dispersing aids, adhesion promoters, flavors, sweeteners, dyes, preservatives and mixtures thereof.

22. A method of making a cosmetic composition comprising admixing a cosmetic ingredient with a readily dispersible perfusion product, wherein said readily dispersible perfusion product comprises a matrix formed by subjecting a feedstock material comprising a carbohydrate carrier material and a perfluoro compound to flash-flow conditions which alter the physical and/or chemical structure of said carrier material to form said product which is water-dispersible, such that upon addition to a dispersing medium free from any emulsifying agent, said product forms a colloidal dispersion in the dispersing medium.

23. The method of claim 22, wherein said cosmetic ingredient is selected from the group consisting of dimethyl siloxanes, mucopolysaccharides, methyl paraben, propyl paraben, biotin, lanolin, aloe, mineral oil, nicotinamide compounds, sun screens, hair conditioners, moisturizing agents, astringents, cosmetic powders and mixtures thereof.

24. The method of claim 23, wherein said feedstock material further comprises a member selected from the group consisting of dispersing aids, adhesion promoters, flavors, sweeteners, dyes, preservatives and mixtures thereof.

* * * * *